(12) United States Patent
Akinsanya

(10) Patent No.: US 12,127,818 B2
(45) Date of Patent: Oct. 29, 2024

(54) HEALTH SCAN DEVICE

(71) Applicant: Modupe Akinsanya, Bronx, NY (US)

(72) Inventor: Modupe Akinsanya, Bronx, NY (US)

( * ) Notice: Subject to any disclaimer, the term of this patent is extended or adjusted under 35 U.S.C. 154(b) by 232 days.

(21) Appl. No.: 17/363,159

(22) Filed: Jun. 30, 2021

(65) Prior Publication Data
US 2022/0079458 A1 Mar. 17, 2022

Related U.S. Application Data

(60) Provisional application No. 63/078,929, filed on Sep. 16, 2020.

(51) Int. Cl.
| | |
|---|---|
| *A61B 5/0205* | (2006.01) |
| *A01N 31/14* | (2006.01) |
| *A61B 5/00* | (2006.01) |
| *A61B 5/024* | (2006.01) |
| *A61B 5/1455* | (2006.01) |
| *A61B 5/332* | (2021.01) |

(52) U.S. Cl.
CPC .......... *A61B 5/02055* (2013.01); *A01N 31/14* (2013.01); *A61B 5/0022* (2013.01); *A61B 5/02427* (2013.01); *A61B 5/14552* (2013.01); *A61B 5/332* (2021.01); *A61B 5/6825* (2013.01); *A61B 5/742* (2013.01); *A61B 5/746* (2013.01); *A61B 5/748* (2013.01); *A61B 2560/0431* (2013.01)

(58) Field of Classification Search
CPC ............ A61B 5/02055; A61B 5/02427; A61B 5/14552; A61B 5/332; A61B 5/742; A61B 5/746; A61B 5/748; A61B 2560/0431; H04N 1/00244; H04N 2201/0082; A01P 1/00
See application file for complete search history.

(56) References Cited

U.S. PATENT DOCUMENTS

| | | | |
|---|---|---|---|
| 9,574,060 B2 * | 2/2017 | Bui ............................ | C08J 9/36 |
| 2004/0225533 A1 * | 11/2004 | Cosentino .............. | G16H 20/60 |
| | | | 600/300 |
| 2007/0270669 A1 * | 11/2007 | Parnagian .............. | A61B 5/339 |
| | | | 600/301 |
| 2008/0086817 A1 * | 4/2008 | Zucker ................. | A61G 7/0504 |
| | | | 5/603 |

(Continued)

FOREIGN PATENT DOCUMENTS

WO WO-2011031061 A2 * 3/2011 ............... A61B 5/02

*Primary Examiner* — James M Kish
*Assistant Examiner* — Roland Dinga
(74) *Attorney, Agent, or Firm* — Brennan, Manna & Diamond, LLC

(57) ABSTRACT

This present invention relates to a body scanning device that is capable of both capturing, displaying and/or transmitting to remote locations the vital signs of a user and a preliminary diagnosis. More specifically, the body scanning device scans a palm of an individual using an electrical pulse to read and interpret the individual's vital signs, as well as allowing the user to input body parameter information such as sex, height, weight, etc. The body scanning device provides the individual with diagnostic questions, and an overall diagnosis based on the scan. The body scanning device is further comprised of Wi-Fi and/or Bluetooth capabilities.

16 Claims, 4 Drawing Sheets

(56) References Cited

U.S. PATENT DOCUMENTS

| | | | | |
|---|---|---|---|---|
| 2010/0298718 A1* | 11/2010 | Gilham | ................ | H04W 16/10 |
| | | | | 600/484 |
| 2011/0200236 A1* | 8/2011 | Roemen | ................ | G06V 40/10 |
| | | | | 382/124 |
| 2014/0296686 A1* | 10/2014 | Konchitsky | .............. | A61B 5/25 |
| | | | | 600/393 |
| 2015/0070319 A1* | 3/2015 | Pryor | ..................... | G06V 20/56 |
| | | | | 345/175 |
| 2016/0135736 A1* | 5/2016 | Bowers | ................ | A61B 5/7465 |
| | | | | 704/270 |
| 2017/0188864 A1* | 7/2017 | Drury | ................ | A61B 5/02427 |
| 2018/0092308 A1* | 4/2018 | Barber, III | ............. | A23B 7/015 |
| 2020/0229765 A1* | 7/2020 | Peabody | ............ | A61B 5/14532 |

\* cited by examiner

HEALTH SCAN DEVICE

CROSS-REFERENCE TO RELATED APPLICATION

The present application claims priority to, and the benefit of, U.S. Provisional Application No. 63/078,929, which was filed on Sep. 16, 2020 and is incorporated herein by reference in its entirety.

FIELD OF THE INVENTION

The present invention relates generally to the field of health monitoring. More specifically, the present invention relates to a body scanning device used to identify potential health issues through measurement of pulse, blood pressure, stress level and other vital statistics. The body health scanner device allows a user to place his or her palm on the surface of the device, which scans the body vitals through an electrical pulse. Further, the health scanner device features wireless communication technologies such as Wi-Fi, Bluetooth, or the like, to print the scanned health information directly from the scanner device to a nearby printer or other output. Accordingly, the present disclosure makes specific reference thereto. Nonetheless, it is to be appreciated that aspects of the present invention are also equally applicable to other like applications, devices and methods of manufacture.

BACKGROUND OF THE INVENTION

By way of background, people suffer from various diseases around the world, and if left undetected, many of the diseases may lead to various health complications or even death. Furthermore, healthcare technology has evolved over the years to detect symptoms of individuals suffering from different diseases, and various medical devices are available that enable doctors and other healthcare workers to diagnose said diseases. The early and correct diagnosis of a disease is recommended for the timely treatment thereof, and to prevent further health complications and fatalities.

Many individuals become ill and are unaware of what is wrong with their bodies due to a lack of available information about their symptoms. For diagnosis, people usually visit health care centers for health checkups, and to get the advice of a doctor. Various medical tests may be suggested to detect a disease or ailment of the person. Once the illness is diagnosed, the treatment of the person can be started. Further, multiple visits to the healthcare centers would typically be required if the illness is not detected during the initial visit. However, checkups at a healthcare center can be quite expensive, and not every individual can afford the cost of checkup at such centers. Further, some individuals may not be able to afford multiple doctor visits if they cannot diagnose the disease in a single patient encounter. Still other individuals may ignore their symptoms initially to avoid the expense of the healthcare centers, which could lead to further complications in the future.

Therefore, there exists a long felt need in the art for a health scanning device that enables an individual to measure and monitor their personal health data. More specifically, there is a long felt need in the art for a health scanning tool which measures the vital statistics of the user without a health worker present including, without limitation, pulse, blood pressure, stress level, etc., and allows the user to easily print out the same. Additionally, there is a long felt need in the art for a health scanning device which assesses the health level of the user, and provides diagnostic information. Moreover, there is long felt need in the art for a health scanning device that supports wireless communication technology, thereby making the scanned information more accessible to both the user and his or her healthcare professionals. Finally, there is a long felt need in the art for a health scanning device that is relatively inexpensive to manufacture, and that is both safe and easy to use.

The subject matter disclosed and claimed herein, in one embodiment thereof, comprises a portable, human vital sign scanning device to identify potential health issues of the user. The device comprises a scanning surface on which a user places his or her palm for scanning, a scanner for scanning the palm of the user placed on the scanning surface using an electrical pulse, wherein the scanner includes a plurality of sensors to measure temperature, ECG, heart rate, pulse oximetry or SpO2 and blood pressure. The type of sensors used in any particular health scanning device may vary depending upon user need and/or preference. The sensors are connected to a processor, and a touch pad input surface for inputting body parameter information such as gender, height and weight. The touch pad input also provides a user with one or more diagnostic questions for the user to input responses to the queries. The responses can be used to adapt some of the sensor input or output. A wireless communication module is used for transmitting the vital sign information to a wirelessly connected device, such as a printer and/or electronic device, as well as to a remote location where a healthcare provider may receive the information and arrange for immediate care or an ambulance if the statistics show an exigent situation exists. Finally, a memory is provided for storing instructions which are executed by the processor to print the scanned vital sign information to easily present to healthcare providers.

In this manner, the novel health scanning device of the present invention accomplishes all of the forgoing objectives, and provides a relatively affordable, easy and convenient solution for measuring vital parameters of an individual without the presence of a healthcare professional. The health scanning device of the present invention is also user friendly, inasmuch as it is more convenient to use than its alternatives, and does not require the user to visit a healthcare center to obtain an early diagnosis of a disease. Additionally, the health scanning device enables the user to print the scanned health results for ready use at a healthcare center for further treatment.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a portable human vital sign scanning device to identify potential health issues. The device comprises a scanning surface upon which a user places his or her palm to be scanned, which is preferably positioned along the top surface of the device. The scanning surface may be formed or treated with an antimicrobial, antifungal or other disease or germ eradicating material (i.e., 99.9% effective) so as to avoid the spread of disease or contamination amongst various users. Further, the scanning surface utilizes an electric pulse and a plurality of sensors to scan and analyze the user's palm. The sensors may include, but are not limited to, a temperature sensor, ECG sensor, heart rate sensor, pulse oximetry sensor, blood pressure sensor, etc. The sensors are in turn connected to a processor and a touch pad input surface that enables the user to input certain body parameter information including, without limitation, the user's gender, height, weight, etc. The information input into the processor can then be used to extract threshold information about the vital signs to be collected from the user from the device's memory for use in making a comparison between the collected data and normal health parameters. The touch pad input also provides a user with the ability to answer a series of diagnostic questions that may also be analyzed by the processor.

In a preferred embodiment of the present invention the health scanning device further comprises a memory and a wireless communication module for transmitting the user's vital signs and other diagnostic information to a remote device such as a printer, electronic device, remote monitoring site, healthcare worker, medical center, etc. The memory is useful for storing, among other things, medical information that enables the processor to make an initial diagnosis, instructions which may be executed by the processor to print the scanned vital sign information to easily present to a healthcare provider, and threshold information which can result in an alarm indicator being triggered if one or more of the vital signs are outside of an acceptable range of vital signs for a user.

In a further embodiment of the present invention, a portable body scanning tool is disclosed. The portable scanning tool comprises a combination of a vital sign scanner and an associated printer. The portable vital sign scanner includes a touch surface or touch pad to input body parameters such as the user's sex, age, height, weight, etc., and a scanner for scanning a user's palm to obtain certain vital signs such as, but not limited to, pulse, blood pressure, stress level, etc. The scan is accomplished via an electrical pulse when the user's palm is placed onto the touch surface. For example, the scanning surface is capable of scanning the radial pulse of an individual to determine the level of his or her stress. Further, the scanner comprises a wireless communication module for wirelessly communicating the collected information to the printer. In one embodiment, the vital sign scanner further includes rechargeable batteries to power the scanner device, a USB port for charging the batteries and an ethernet port to connect to a router for accessing the internet. The vital sign scanner may further comprise one or more of an ECG electrode, a temperature sensor and/or a photoplethysmogram (PPG) sensor, which is an optically obtained plethysmogram that can be used to detect blood volume changes in the microvascular bed of tissue. The various sensors are used to detect the vital signs of the user whose palm is placed onto the touch surface of the scanner device and scanned.

In yet another embodiment of the present invention, a non-invasive and non-wearable human vital sign scanner device for reading a user's vital signs is disclosed. The device comprises a scanner, a processor and a memory for storing instructions to be executed by the processor and for sending recorded vital signs information to a connected printer. More specifically, the scanner records the vital signs of a user by scanning his or her palm via an electrical pulse when the palm is placed on a surface of the scanner device. The signal processor is provided to execute the signal processing instructions stored in the memory to correctly output the recorded vital signs for the display and render a printed output.

In yet another embodiment of the present invention, a method of obtaining a plurality of vital signs from a user with a portable vital sign scanner device is disclosed and comprises the initial step of switching on the portable vital sign scanner device using a power control. Next, body parameters such as the user's sex, age, height and weight are inputted into the device by a user via a touch keypad shown on a top surface of the scanning device. The user then places his or her palm on the scanning surface of the scanner device, wherein the palm of the user is scanned via an electrical pulse and the collected vital signs of the user are recorded in the memory of the device. Diagnostic questions may also be shown on the scanning surface for the user to respond. The recorded vital signs are then processed based on the received input, and the recorded vital sign information is transmitted to a wirelessly connected printer. The vital sign information is rendered or printed by the printer for presentation to a healthcare provider or the individual utilizing the scanner. The vital sign information may also be transmitted in the form of a report to an email address input by the user and/or to a healthcare provider whose profile is authorized by the scanner device.

In a further embodiment, the portable vital sign scanner device shows a vital sign scan progress bar and provides a visual and/or audible alert to indicate a successful completion of the scan of the palm of the user. Also, the portable vital sign scanner device may indicate the correct position of the palm on the scanning surface prior to the scan being initiated. The indication may be in the form of a palm shaped design or outline within which the user needs to place his or her palm for a successful scan of the user's vital signs. In a further embodiment, the portable vital sign scanner device may be wirelessly connected to a server at a hospital or a clinic where the recorded vital signs are uploaded for review and consultation by a medical practitioner.

The portable health scan device of the present invention is advantageous because it provides a self-monitoring and a non-invasive method of detecting a user's vital signs without the need for a healthcare worker to be present. More specifically, the user does not need to wait for a medical professional or other health care worker to measure and/or record the vital signs of the user, or incur the expense typically associated with an in person visit. Further, the scanning device is both portable and relatively lightweight, and the scanned vital sign information is easily printed along with preliminary recommendations based on the results of the scan and other inputted information. For example, irregularities in the scanned data can be determined or identified by comparing the data generated with certain threshold information stored in the memory of the device.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE INVENTION

Figure 1:
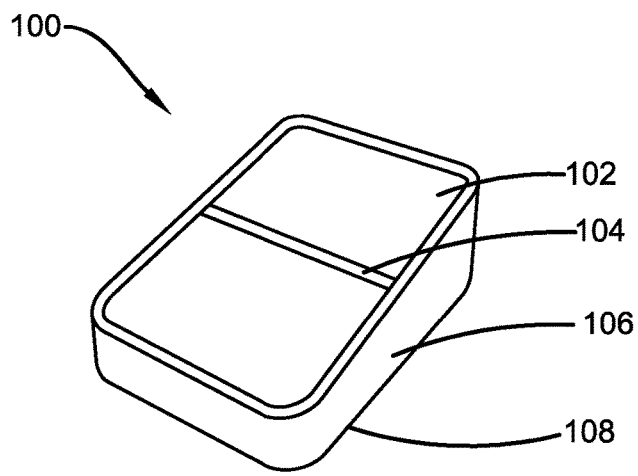
FIG. 1 illustrates a perspective view of one potential embodiment of a portable vital sign scanner device of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long felt need in the art for a health scanning device that enables an individual to measure and monitor his or her personal health data without the need for a healthcare worker to be present, wherein the health data being monitored and gathered includes, without limitation, the individual's pulse, blood pressure, stress level, etc. Additionally, there is a long felt need in the art for a health scanning device that assesses the vital signs of the individual, provides preliminary diagnostic information based on the assessment, and enables the individual to easily and quickly transmit the results and preliminary diagnostic information to a host of different devices including, without limitation, a printer, storage medium, server, healthcare provider or facility, etc. Finally, there is a long felt need in the art for a health scanning device that is relatively inexpensive to manufacture, and that is both safe and easy to use.

Referring initially to the drawings, FIG. 1 illustrates a perspective view of one potential embodiment of a portable vital sign scanner device 100 of the present invention in accordance with the disclosed architecture. More specifically, the portable vital sign scanner device 100 is a body scanning tool that is used to identify potential health issues, and is generally rectangular in shape and comprised of a top scanning surface 102 upon which a user places his or her palm for scanning. The top scanning surface 102 upon which the user places his or her palm or the device 100 itself may further comprise anti-viral chemicals, such as triclosan, and available in product offerings such as Microban®, which may be incorporated into the molding or manufacturing of the device 100 in an effort to prevent the transmission of disease, germs, bacteria and other harmful microbes.

The scanner device 100 rests on a bottom surface 108 which also has a battery compartment for inserting rechargeable or other types of batteries. The top surface 102 is a generally planar surface, and when a user places his or her palm on the top surface 102 to be diagnosed, an electrical pulse 104 is generated and scans the palm of the user to record the vital signs of the user. The top surface 102 is a touch surface, and may also act as a touch-based input device allowing the user to input body parameter information such as, but not limited to, the user's sex, height, weight, name, address, email and other contact information. The top surface 102 can also provide the user with diagnostic questions to which the user can respond using the touch-based input. For example, such questions may include whether the individual is experiencing pain. Nonetheless, the scanner will scan the body regardless of the answer because, even if the answer is no, the individual may not know whether there are abnormalities in the body and the scanner will highlight where the abnormalities are found on the print out. Under the top surface 102, an electronic scanning mechanism is provided and is connected to a plurality of sensors 106 that are used for scanning the palm of the individual.

In the preferred embodiment, the sensors 106 may include one or more of an ECG electrode, a temperature sensor, a SpO2 sensor, a PPG sensor and any other sensor that is capable of sensing and recording a condition or other information pertaining to the user's body, such as a diabetic reading. More specifically, when the user's palm is scanned, the various sensors 106 record the corresponding vital signs of the user and record the same in the memory of the device 100, as explained more fully below.

The portable vital sign scanner device 100 is both portable and relatively lightweight, and is capable of wirelessly communicating with a plurality of electronic devices including, without limitation, a smart phone, computer, tablet, printer, remote server, etc. Once a successful scan is completed for an individual, the portable vital sign scanner device 100 may give a visual and/or audible notification to the user indicating that he or she may remove their hand from the device 100. Similarly, a notification may also be provided upon the completion of an unsuccessful scan. The portable vital sign scanner device 100 is powered ON by a manual power button 109 present on the scanner device 100 and is powered OFF automatically after a predetermined time of inactivity, or manually through the manual power button 109.

Figure 2:
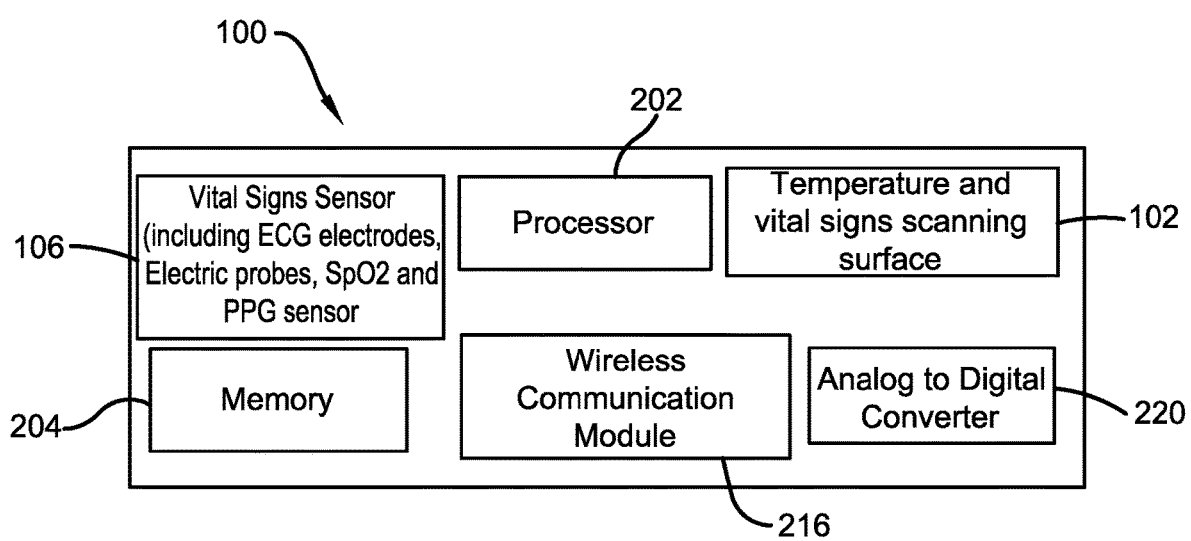
FIG. 2 illustrates a block diagram showing the various components of one potential embodiment of the portable vital sign scanner device of the present invention in accordance with the disclosed architecture.

FIG. 2 illustrates a block diagram showing the various components of one potential embodiment of the portable vital sign scanner device 100 of the present invention in accordance with the disclosed architecture. More specifically, the portable vital sign scanner device 100 is comprised of the scanning surface 102, the plurality of sensors 106, a processor 202, a memory 204, a wireless communication module 216 and an analog to digital converter 220. The processor 202 performs the execution of the instructions present in the memory 204 of the scanner device 100, and also controls the operation of the various components of the scanner device 100. The memory 204 stores the instructions to print the scanned vital signs, and also stores the diagnostic questions to be asked of the user, the user's responses and other medical and diagnostic information. For example, the memory 204 may also contain threshold information to compare the vital signs of the user against normal or healthy parameters, and can provide information on whether an alarm should be triggered to alert the user of an abnormality in the collected vital signs.

As stated above, the memory 204 also stores the user inputted information as well as the vital sign information gathered by the plurality of sensors 106 built into the scanner. More specifically, the vital signs sensors 106, such as ECG electrodes, an electric probe for temperature measurement, and SpO2 and PPG sensors, are present in the scanner device 100 to measure the vital signs of the individual who has placed his or her palm on top scanning surface 102 of the scanner device 100. The processor 202 also processes the vital signs recorded by the vital sign sensors 106 to derive insights and recommendations by comparing the data captured to threshold values stored in the memory 204 and alerting the user to any abnormalities that may warrant further medical attention.

Each of the various sensors are commercially available. For example, the built-in temperature sensor will read through the whole body to determine whether the body temperature is low, moderate, high or too high, and the EKG sensor will sense the electrical activity of the heart and a streamlined path to cardiac diagnosis to determine whether the heart rate is tachycardia or bradycardia. Likewise, the heart rate sensor will measures the heart rate in beats per minute, and the blood pressure sensor makes it easy measure the individual's blood pressure, both the systolic and diastolic. Finally, the pulse oximeter sensor measures the aggregate of oxygen in the individual's blood.

A second removable memory (not shown) can also be added to the scanner device 100 in addition to the memory 204 for storing the user data and vital sign information. Either of the memories 204 may be volatile (i.e., requiring power) or non-volatile (i.e., not requiring power). A wireless communication module 216 in the form of a Bluetooth/Wi-Fi SoC is also present in the scanner device 100 to establish wireless communication channels to a portable device, such as a smart phone, computer, tablet, printer, remote server at a healthcare facility, etc. For example, the processor 202 may execute instructions to send the user's vital sign information, preliminary diagnosis, etc., to the wireless printer for printing, or to a health care professional to facilitate follow-up medical care. To show and print the recorded vital signs in digital signals and representation, an analog to digital converter 220 may also be embedded in the scanner device 100 of the present invention. More specifically, the processor 202 processes the vital signs and the same are converted into digital form by an analog to digital converter 220.

Figure 3:
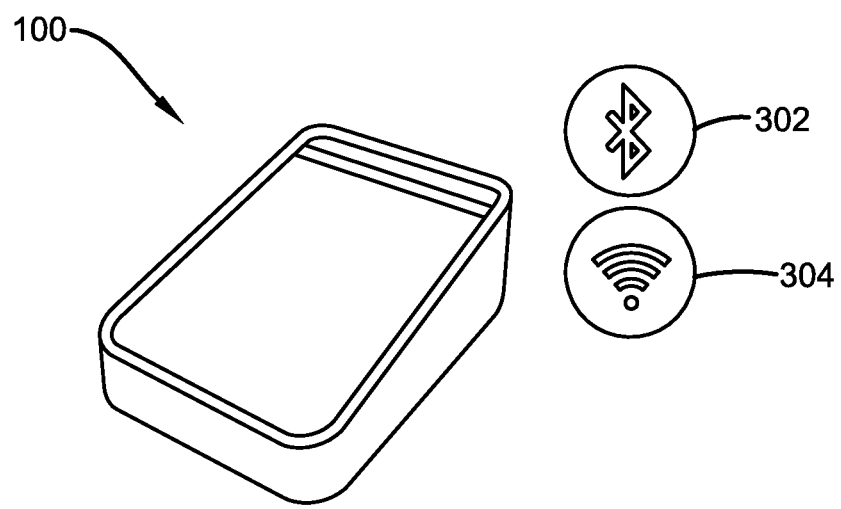
FIG. 3 illustrates the Bluetooth and Wi-Fi capabilities of one potential embodiment of the portable vital sign scanner device of the present invention in accordance with the disclosed architecture.

FIG. 3 illustrates the Bluetooth and Wi-Fi capabilities of one potential embodiment of the portable vital sign scanner device 100 of the present invention in accordance with the disclosed architecture. More specifically, the wireless communication module 216 of the portable vital sign scanner device 100 may connect wirelessly to a router through built-in Wi-Fi capability 302 and/or to a remote electronic device or a printer through a Wi-Fi Direct communication protocol. The portable vital sign scanner device 100 also has Bluetooth capability 304, which can be used to establish wireless communication channel with a printer, electronic device such as smartphone, wireless display etc.

Figure 4:
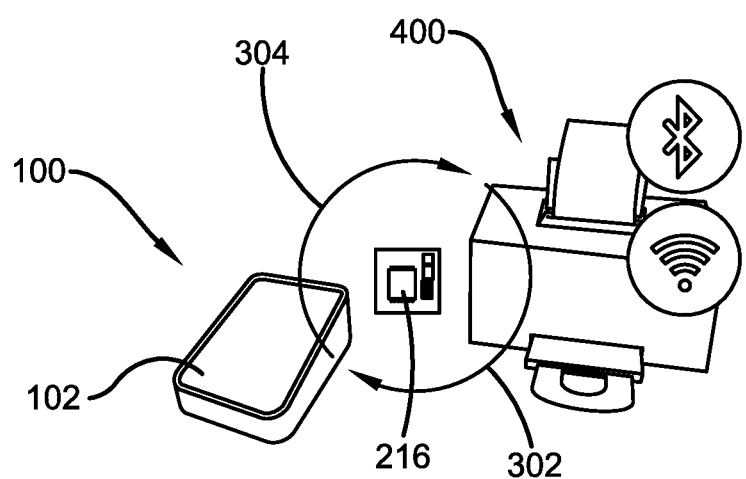
FIG. 4 illustrates a perspective view of one potential embodiment of a portable vital sign scanner device of the present invention in accordance with the disclosed architecture, wherein the device is wirelessly communicating with a printer.

FIG. 4 illustrates a perspective view of one potential embodiment of a portable vital sign scanner device 100 of the present invention in accordance with the disclosed architecture, wherein the device 100 is wirelessly communicating with a printer 400. More specifically, the scanner device 100 has a built-in wireless communication module 216 which establishes a Wi-Fi based communication channel 304 or a Bluetooth based communication channel 302 between the scanner device 100 and the wireless printer 400. Once the scanner device 100 is switched on, nearby discoverable devices, such as the printer 400, are identified on the top surface 102 of the scanner device 100. When an ancillary device, such as the printer 400, is selected, a wireless communication channel is set up between the scanner device 100 and a wireless printer 400.

In one embodiment, the wired connection can be established between the scanner device 100 and the printer 400, wherein the scanner device 100 features 802.11a/b/g/n/ac/ax. Once a successful scan is completed for a user, an automatic command is sent by the processor 202 of the scanner device 100 to the printer 400 to print the measured vital signs of the user. Using the Wi-Fi capability, the vital sign information may also be sent to a remote server/cloud-based server of a hospital or clinic for a medical practitioner to readily view and store the records for future purposes.

Figure 5:
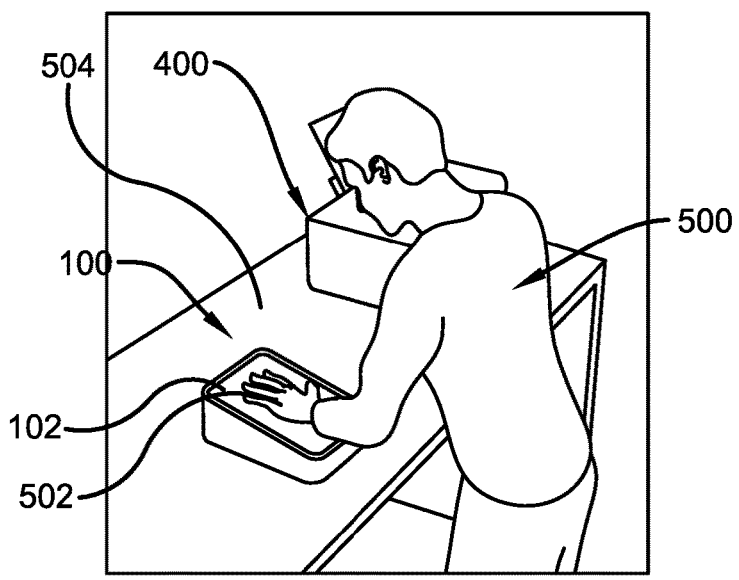
FIG. 5 illustrates a perspective view of one potential embodiment of a portable vital sign scanner device of the present invention in accordance with the disclosed architecture, wherein a user is using the device and a wireless printer to obtain a printout of his vital signs to, for example, share with a medical professional.

FIG. 5 illustrates a perspective view of one potential embodiment of a portable vital sign scanner device 100 of the present invention in accordance with the disclosed architecture, wherein a user 500 is using the device 100 and a wireless printer 400 to obtain a printout of his vital signs to, for example, share with a medical professional (not shown). More specifically, to use the scanner device 100 after it is turned on, the user 500 will places his or her palm 502 of either the right or left hand on top of the scanning surface 102, which may be placed on a table or other suitable surface 504. Once a successful scanning is complete for the user 500 by the electronic pulse of the scanner device 100, a print command is given to the printer 400 to print the measured vital signs of the user 500. The user 500 needs to simply place his or her palm 502 on the surface 102 of the scanner device 100 for body vitals to be scanned through an electrical pulse, and the scanner device 100 provides an audible and/or visual notification to the user 500 upon successful completion of the scan to indicate that the individual may remove his or her hand.

Figure 6:
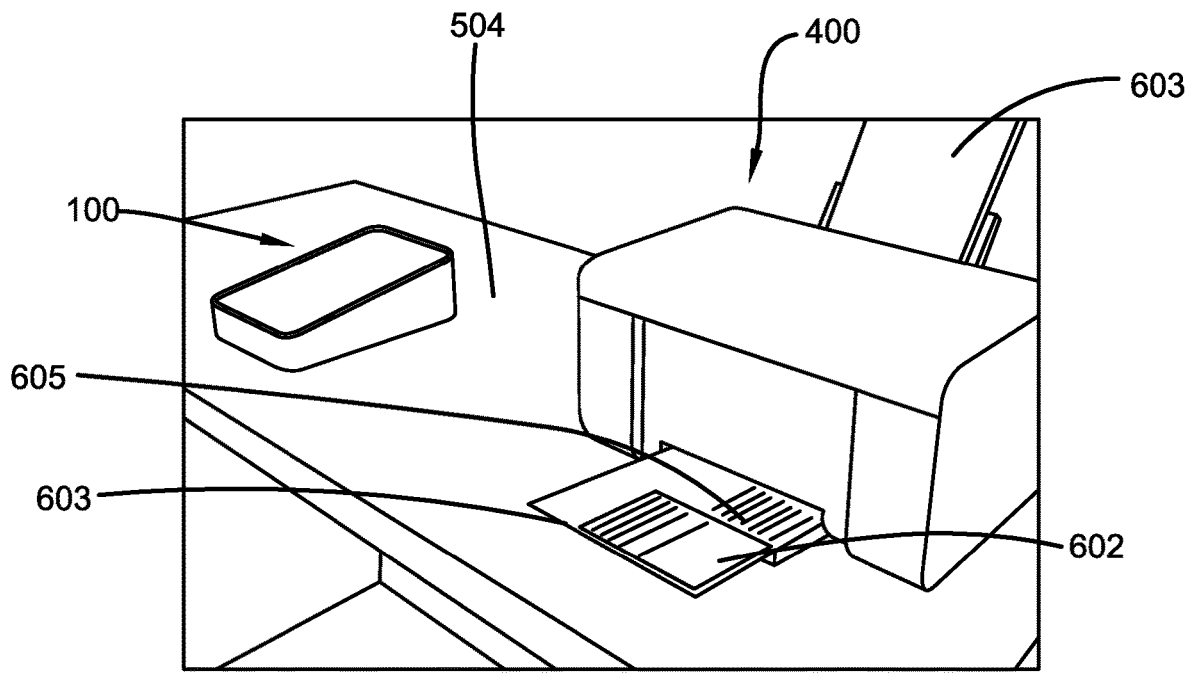
FIG. 6 illustrates a perspective view of one potential embodiment of a portable vital sign scanner device of the present invention in accordance with the disclosed architecture, wherein the device is wirelessly communicating with a printer to create a printout for the user.

FIG. 6 illustrates another perspective view of one potential embodiment of a portable vital sign scanner device 100 of the present invention in accordance with the disclosed architecture, wherein the device 100 is wirelessly communicating with a printer 400 to create a printout for the user 500. More specifically, once the scan has been successfully completed, an automatic print command, or upon a manual instruction from a print button on the scanner device 100, the collected vital signs are printed 602 by a connected printer 400 connected wirelessly through Wi-Fi/Bluetooth/Wi-Fi Direct. The printed form 602 may have predefined areas for different types of data 603, 605. For example, the data may be displayed in a graphical configuration 603 and/or in a textual format 605.

Figure 7:
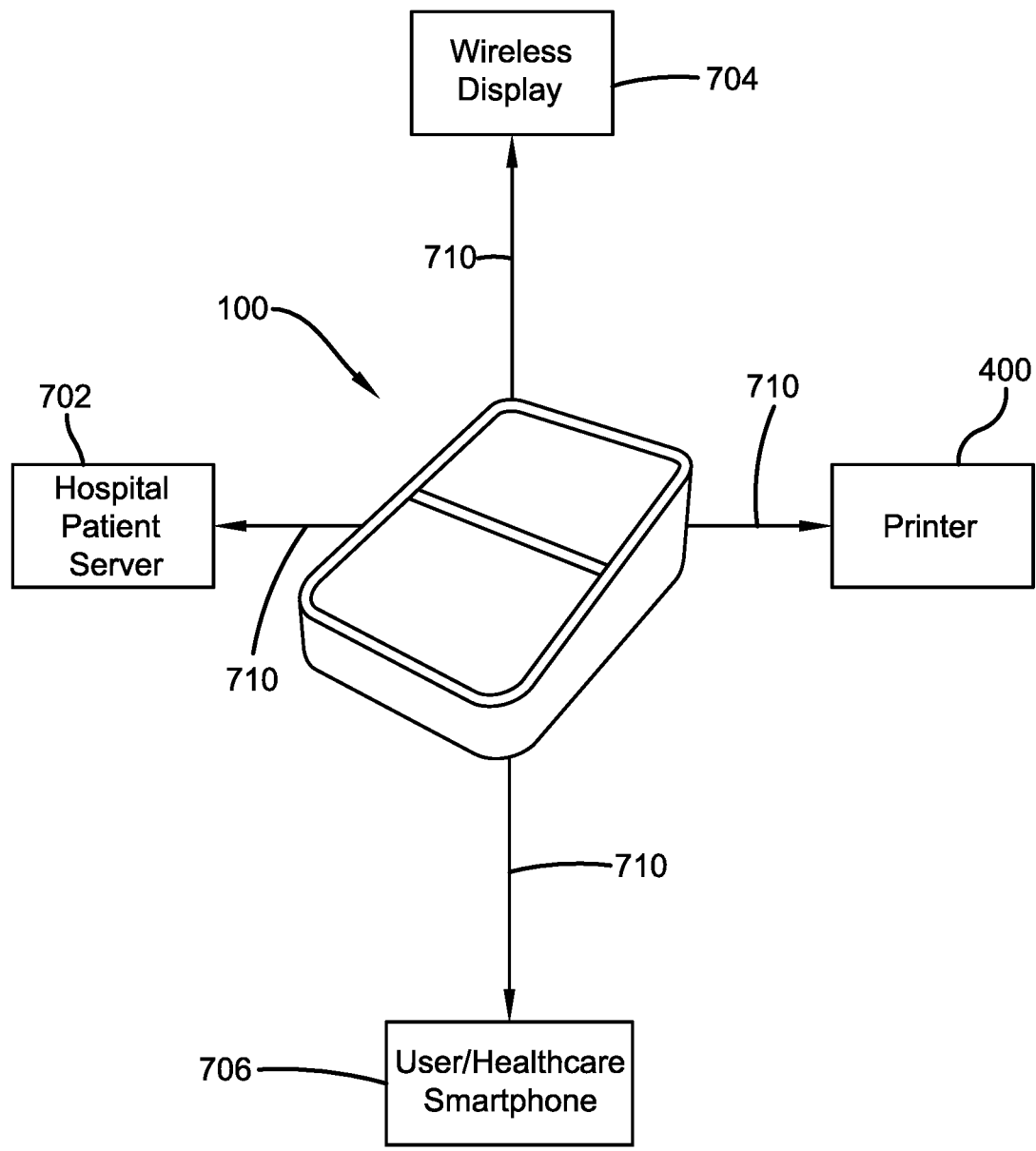
FIG. 7 illustrates a diagrammatic view of one potential embodiment of a portable vital sign scanner device of the present invention wirelessly communicating with a plurality of devices in accordance with the disclosed architecture.

FIG. 7 illustrates a diagrammatic view of one potential embodiment of a portable vital sign scanner device 100 of the present invention wirelessly communicating with a plurality of devices in accordance with the disclosed architecture. More specifically, the scanner device 100 is capable of connecting with one or more devices to provide accurate vital sign information quickly and without requiring the user to visit a medical facility or see a healthcare professional. Through a wireless channel 710, the scanner device 100 may connect to a printer 400 for: (a) printing of the vital sign records; (b) transmitting of information to a wireless display 704 to display the vital sign information; (c) sending the information in the form of a report to a paired or authorized smartphone 706; and/or (d) uploading the vital sign information to a medical database at a server 702 of a hospital or a clinic.

In an embodiment of the present invention, the portable vital sign scanner device 100 of the present invention can be of any other shape such as square, diamond, circular or others, as per the desires of the user. Further, the vital sign scanner device 100 may have a mounting loop or other attachment device at the back of the device 100 to allow it to be mounted on a wall at a predetermined height, such that every user can easily scan his or her palm without any discomfort. Other attachment features include an adhesive, hook and loop type fasteners, etc.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "portable vital sign scanner device", "scanner device", "scanning tool", and "full-body scanning tool" are interchangeable and refer to the portable vital sign scanner device 100 of the present invention.

Notwithstanding the forgoing, the portable vital sign scanner device 100 of the present invention can be of any suitable size and configuration as is known in the art without affecting the overall concept of the invention, provided that it accomplishes the above stated objectives. One of ordinary skill in the art will appreciate that the size, configuration and material of the portable vital sign scanner device 100 as shown in the FIGS. are for illustrative purposes only, and that many other sizes and shapes of the portable vital sign scanner device 100 are well within the scope of the present disclosure. Although the dimensions of the portable vital sign scanner device 100 are important design parameters for user convenience, the portable vital sign scanner device 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A health scan device comprising;
a housing sized and configured to receive a palm of an individual;
a scanning surface configured to gather at least one vital sign of the individual via the palm;
a processor;
a volatile memory for storing one or more diagnostic questions and the gathered at least one vital sign;
a removable non-volatile memory; and
wherein the processor is configured to (i) display the one or more diagnostic questions for the individual on the scanning surface, (il) receive one or more user responses from the individual for the displayed one or more diagnostic questions, (iii) generate at least one recommendation including preliminary diagnosis based on processing of the received one or more user responses and the gathered at least one vital sign, and (iv) select and communicate with a health care professional for follow-up medical care for the individual;
an output device for generating a display based on a plurality of information received from the processor; and
wherein the scanning surface is configured to provide a diabetic reading; and
wherein the housing includes an antifungal treatment; and
wherein the health scan device is configured to provide a first visual and audible notification of a successful scan and a second visual and audible notification of an unsuccessful scan; and
wherein the output device is a printer and the display is a printed form generated by the printer and comprising a plurality of predetermined data areas comprising at least one graphical configuration and at least one textual format; and
wherein the housing comprises an adhesive mount for mounting the health scan device on a wall.

2. The health scan device as recited in claim 1, wherein the housing further includes an antimicrobial treatment.

3. The health scan device as recited in claim 2, wherein the treatment comprises triclosan.

4. The health scan device as recited in claim 1 further comprising a communication module.

5. The health scan device as recited in claim 4, wherein the communication module transmits the plurality of information from the processor to a remote location.

6. The health scan device as recited in claim 1 further comprising a plurality of sensors.

7. The health scan device as recited in claim 6, wherein the plurality of sensors are selected from a group including an ECG electrode, a temperature sensor, a PPG sensor, a pulse oximetry sensor or a combination thereof.

8. The health scan device as recited in claim 6 further comprising a touch pad for entering a data related to the individual.

9. The health scan device as recited in claim 8, wherein the data is compared to a range of threshold data stored in the volatile memory.

10. The health scan device as recited in claim 9 further comprising an alarm.

11. The health scan device as recited in claim 10, wherein the alarm is triggered if the data is outside of the range of threshold data.

12. A scanner for collecting a plurality of vital signs of an individual, wherein the scanner comprises:
- a plurality of sensors contained within a housing, wherein the plurality of sensors comprise an ECG electrode, a temperature sensor, a PPG sensor, and a pulse oximetry sensor;
- a processor connected to the plurality of sensors for processing the plurality of vital signs received from a scan of a palm of the individual;
- a first built-in memory and a second removable memory;
- a communication module in communication with the processor;
- a touch pad;
- an analog to digital converter configured to convert sensor data received from the processor into a digital format;
- an output device;
- a hook and loop fastening system for mounting the housing a wall; and
- wherein said first built-in memory stores one or more diagnostic questions and the plurality of vital signs; and
- wherein the processor is configured to (i) display the one or more diagnostic questions for the individual on the scanning surface, (ii) display a pain scale for the individual on the scanning surface, (iii) receive one or more user responses from the individual for the displayed one or more diagnostic questions and the pain scale, (iv) generate at least one recommendation including preliminary diagnosis based on processing of the received one or more user responses and the plurality of vital signs, and (v) select and communicate with a health care professional for follow-up medical care for the individual; and
- wherein the health scan device is configured to provide a first visual and audible notification of a successful scan and a second visual and audible notification of an unsuccessful scan.

13. The scanner for collecting the plurality of vital signs of an individual as recited in claim 12 further comprising a palm shaped design on an upper surface of the housing for determining proper placement of the palm of the individual.

14. The scanner for collecting the plurality of vital signs of an individual as recited in claim 12, wherein the communication module is in communication with the output device.

15. The scanner for collecting the plurality of vital signs of an individual as recited in claim 14, wherein the output device is a printer that generates both a graphical and a textual representation of the plurality of vital signs.

16. A healthcare scanner comprising:
- a housing comprised of an antimicrobial treatment, an upper surface having an outline of a palm, a bottom for placement of the housing on a surface, and a touch pad;
- a plurality of sensors contained within the housing, wherein the plurality of sensors comprise an ECG electrode, a temperature sensor, a PPG sensor, and a pulse oximetry sensor;
- a processor connected to each of the plurality of sensors for processing a plurality of vital signs received from a scan of the palm of an individual;
- a volatile memory for storing one or more diagnostic questions and the plurality of vital signs;
- a removable non-volatile memory; and
- wherein the processor is configured to (i) display the one or more diagnostic questions for the individual on the scanning surface, (il) receive one or more user responses from the individual for the displayed one or more diagnostic questions, (iii) generate at least one recommendation including preliminary diagnosis based on processing of the received one or more user responses and the plurality of vital signs, and (iv) select and communicate with a health care professional for follow-up medical care for the individual;
- a communication module;
- a printer, wherein the communication module is in communication with each of the processor and the printer;
- a rechargeable battery;
- a USB port;
- an ethernet port to connect to a router via an internet;
- an analog to digital converter; and
- wherein the bottom of the housing comprises a hook and loop fastening system and a mounting loop for mounting the healthcare scanner; and
- wherein the health scan device is configured to provide a first visual and audible notification of a successful scan and a second visual and audible notification of an unsuccessful scan; and
- wherein the printer is configured to generate a printed form comprising a plurality of predetermined data areas comprising at least one graphical configuration and at least one textual format.

\* \* \* \* \*